US010633567B2

(12) United States Patent
Dubois (10) Patent No.: US 10,633,567 B2
(45) Date of Patent: Apr. 28, 2020

(54) HOT MELT ELASTIC ATTACHMENT ADHESIVE FOR LOW TEMPERATURE APPLICATIONS (71) Applicant: KRATON POLYMERS U.S. LLC, Houston, TX (US)

(72) Inventor: Donn Dubois, Houston, TX (US)

(73) Assignee: Kraton Polymers U.S. LLC, Houston, TX (US)

( * ) Notice: Subject to any disclaimer, the term of this patent is extended or adjusted under 35 U.S.C. 154(b) by 684 days.

(21) Appl. No.: 15/337,864

(22) Filed: Oct. 28, 2016

(65) Prior Publication Data
US 2017/0121577 A1 May 4, 2017

Related U.S. Application Data (60) Provisional application No. 62/247,920, filed on Oct. 29, 2015.

(51) Int. Cl.
| | | |
|---|---|---|
| *C09J 153/02* | (2006.01) | |
| *C09J 5/00* | (2006.01) | |
| *C08L 91/00* | (2006.01) | |
| *A61L 15/26* | (2006.01) | |
| *A61F 13/49* | (2006.01) | |
| *A61L 15/58* | (2006.01) | |

(52) U.S. Cl.
CPC ......... *C09J 153/02* (2013.01); *A61F 13/4902* (2013.01); *A61F 13/49011* (2013.01); *A61L 15/26* (2013.01); *A61L 15/585* (2013.01); *C08L 91/00* (2013.01); *C09J 5/00* (2013.01); *A61F 2013/49092* (2013.01); *C09J 2201/61* (2013.01); *C09J 2203/10* (2013.01); *C09J 2453/00* (2013.01)

(58) Field of Classification Search
CPC .................................................. C09J 153/02
See application file for complete search history.

(56) References Cited

U.S. PATENT DOCUMENTS

| | | | |
|---|---|---|---|
| RE27,145 E | | 6/1971 | Jones |
| 4,291,139 A | * | 9/1981 | Halasa ............... C08F 297/044 524/505 |
| 5,024,667 A | | 6/1991 | Malcolm et al. |
| 7,288,590 B2 | | 10/2007 | Lechat et al. |
| 7,307,124 B2 | | 12/2007 | DuBois |
| 8,987,372 B2 | | 3/2015 | Hu et al. |
| 2003/0050395 A1 | | 3/2003 | Morishita et al. |
| 2004/0250952 A1 | | 12/2004 | Lechat et al. |
| 2005/0137312 A1 | | 6/2005 | DuBois |
| 2005/0182183 A1 | | 8/2005 | He et al. |
| 2006/0151901 A1 | | 7/2006 | Leffelaar et al. |
| 2006/0205877 A1 | | 9/2006 | DuBois |
| 2010/0249313 A1 | | 9/2010 | Okazaki et al. |
| 2011/0263782 A1 | | 10/2011 | Dubois |
| 2013/0090421 A1 | * | 4/2013 | Vitrano ............. C09J 123/0853 524/505 |
| 2013/0225752 A1 | | 8/2013 | Tse et al. |
| 2015/0159060 A1 | | 6/2015 | Hu et al. |
| 2015/0175855 A1 | * | 6/2015 | Nakajima ............. C09J 153/02 524/505 |

FOREIGN PATENT DOCUMENTS

| | | |
|---|---|---|
| EP | 0532831 A | 3/1993 |
| EP | 0802251 B1 | 10/2003 |
| EP | 1576068 A | 11/2007 |
| WO | 09102039 B | 2/1991 |

OTHER PUBLICATIONS

Runyon, James R et al., Journal of Applied Polymer Science, 1969, vol. 13, No. 11, p. 2359-2369.

* cited by examiner

*Primary Examiner* — Jeffrey C Mullis
(74) *Attorney, Agent, or Firm* — Ramesh Krishnamurti (57) ABSTRACT

An adhesive composition comprising: one or more block copolymers and one or more tackifying resins, wherein said one or more block copolymers comprise (i) one or more blocks of polymerized alkenyl arene monomer (A block), (ii) one or more blocks of polymerized conjugated diene monomer (B block), and optionally at least one low molecular weight (compared to B block) block of polymerized conjugated diene (C block), where the A, B, and C blocks can vary independent of each other with regard to composition and molecular weight.

16 Claims, 2 Drawing Sheets

HOT MELT ELASTIC ATTACHMENT ADHESIVE FOR LOW TEMPERATURE APPLICATIONS

CROSS-REFERENCE TO RELATED APPLICATIONS

The present application is a non-provisional of and claims priority to U.S. Provisional Patent Application No. 62/247,920 filed Oct. 29, 2015 and entitled "Hot Melt Elastic Attachment Adhesive for Low Temperature Applications," which application is incorporated by reference herein in its entirety.

TECHNICAL FIELD

The present disclosure relates to a hot-melt adhesive for elastic attachment with utility in the production of diaper or hygiene products. Hot melt adhesives of the present disclosure can be applied by spraying at significantly lower temperatures to reduce cost, minimize adhesive degradation and allow application of the adhesive to thin substrates. Typical application temperatures are about 160° C. The present adhesive disclosure can be sprayed at temperatures as low as 125° C. (257° F.).

BACKGROUND

Block copolymers comprising terminal poly(styrene) blocks and one or more central poly(isoprene) blocks, more particularly triblock copolymers, are used in hot-melt adhesive compositions for the manufacture of disposable articles. More specifically triblock copolymers having a poly(styrene) content of from 25 weight percent (wt. %) to 35 wt. % and having a total apparent molecular weight of from 100,000 Daltons (Da or grams/mole (g/mol)) to 300,000 Da are generally used in hot-melt adhesive compositions in the diaper industry in two manners:

1) as assembly adhesive to glue the diaper poly(ethylene) main frame, and
2) as an attachment adhesive to glue the elastic threads (fibers) or films which are used as waist and leg bands.

Suitable adhesives are characteristically clear or lightly colored, low in odor, sprayable as a hot-melt adhesive, show good adhesion to poly(olefin) films and do not strike through the non-woven back sheet. These adhesives also typically display a melt viscosity that allows spray application typically in the temperature range of 160° C. to 180° C. Also another desirable quality of these adhesives is that they are relatively inexpensive.

Elastic attachment adhesive is used to adhere elastic threads to polyethylene and non-woven films in order to form an elastic waist or leg band for diaper or hygiene products. Multiple strands of elastic threads are elongated, commonly 300%, and coated with adhesive composition at a temperature of about 160° C. to 180° C. just prior to being pinched inside of the poly(olefin) and non-woven films. Like construction adhesives, they are usually sprayed in a variety of patterns such as spiral or wrap-around patterns. When the ends of the elastic are cut later in the process, the composite contracts causing the non-woven and poly(olefin) films to pucker to form an elastic band.

Although specifically designed block copolymers show an acceptable hot-melt viscosity/temperature profile and have a sufficiently low viscosity at the usually applied hot-melt temperatures of up to 180° C. thereby enabling efficient processing, there is still an economic need for block copolymers which demonstrate processing efficiency, in combination with other attractive properties noted hereinbefore.

The physical requirements for an elastic attachment adhesive are:

1) high cohesive strength and good creep resistance;
2) ability to adhere strongly to polyethylene and polypropylene non-woven films in addition to more polar elastic like polyurethane;
3) low melt viscosity and consequently a high melt flow rate—low temperature application typically requires a viscosity range of about 10,000 centipoise (cps) to 15,000 cps at spray nozzle temperature;
4) sufficient melt viscosity balanced against maintaining sufficient pump pressure; and
5) high melt strength for spray applications.

It will be appreciated that a relatively low hot-melt viscosity facilitates a high production speed in a diaper manufacturing line without the production of significant amounts of off specification product. Problems which normally cause such off specification product may be, for example, adhesive viscosity degradation, adhesive discoloration, damage to the polyethylene film or formation of char. Accordingly, developmental efforts in diaper manufacture continue today with down-gauging of polyolefin films and elastic threads which require a spray application temperature as low as possible while still maintaining adequate adhesion and creep resistance The present disclosure provides improved adhesive compositions which show a reasonable viscosity at temperatures in the range of from about 125° C. to about 140° C. in order to avoid the hereinbefore mentioned problems while allowing sprayability at higher production speeds.

SUMMARY

Disclosed herein is an adhesive composition comprising: one or more block copolymers and one or more tackifying resins, wherein said one or more block copolymers comprise (i) one or more blocks of polymerized alkenyl arene monomer (A block), (ii) one or more blocks of polymerized conjugated diene monomer (B block), and optionally at least one low molecular weight (compared to B block) block of polymerized conjugated diene (C block), where the A, B, and C blocks can vary independent of each other with regard to composition and molecular weight.

Also disclosed herein is a diaper having leg and waist holes for humans comprising elastic attachments around the leg and waist holes of the diaper, the elastic attachment being secured to the diaper by means of an adhesive composition, the adhesive composition comprising one or more block copolymers wherein said one or more block copolymers comprise (i) one or more blocks of polymerized alkenyl arene monomer (A block), (ii) one or more blocks of polymerized conjugated diene monomer (B block), and optionally at least one low molecular weight (compared to B block) block of polymerized conjugated diene (C block), where the A, B, and C blocks can vary independent of each other with regard to composition and molecular weight, one or more end block resins, one or more tackifiers, and one or more oils, wherein the block copolymer is present in a range from about 10 to about 30 wt. %, the tackifier is present in a range from about 25 wt. % to about 70 wt. %, the one or more end block resins are present in a range of about 10 wt. % to about 40 wt. %, and the one or more oils are present in a range of about 5 wt. % to about 30 wt. % based on the total weight of the adhesive composition.

DETAILED DESCRIPTION

The main components used in the adhesive compositions of the present disclosure are a block copolymer (component 1), one or more tackifying resins (or combination of resins) (component 2), a plasticizer (component 3) and antioxidants (component 4). In an aspect, a composition of the present disclosure further comprises an optional alkenyl arene homo- or copolymer (component 5). It is noted that the block copolymer itself has an alkenyl arene polymer block. This is not to be confused with optional component 5 that contains no other component of the block copolymer (component 1).

The block copolymer (component 1) of the present disclosure is represented by structures containing block (A) of a polymerized alkenyl arene monomer or a mixture of polymerized alkenyl arene monomers, and block (B) of a polymerized conjugated diene monomer or a mixture of polymerized conjugated diene monomers. Block C is an optional low molecular weight (compared to block (B)) polymerized conjugated diene or a mixture of polymerized conjugated dienes. Suitable structures are: A-B-A, made by sequential polymerization; $(AB)_nX$, where n=2–20, X is a coupling agent fragment, and some uncoupled diblock AB will remain; A-B-A-C, made by sequential polymerization; C-A-B-A-C, made by sequential polymerization; $(C-A-B)_nX$, where n=2–20, X is a coupling agent fragment, and some uncoupled triblock CAB will remain; $(A-B)_nX(C)_m$, where n=1–20, m=1–20, X is a coupling agent fragment, and some uncoupled C and AB diblock will remain and the sum of n+m cannot be greater than the valence of the coupling agent; and $(C-A-B)_nX(C)_m$, where n is a rational number from 1 to 20, m is a rational number from 1 to 20, X is a coupling agent fragment, and some uncoupled C and CAB triblock will remain, and the sum of n+m cannot be greater than the valence of the coupling agent. If the coupling agent is capable of polymerization (such as divinyl benzene) then the valence requirement does not apply. For all the above structures, each of the A, B and C blocks can vary independent of the other A, B and C blocks with regard to composition and molecular weight.

The (A) blocks of the polymerized alkenyl arene monomer can be styrene, alpha-methylstyrene, para-methylstyrene, vinyl toluene, vinyl naphthalene, para-butyl styrene or combinations thereof. In an aspect, the A block is formed from the polymerization of styrene. The A blocks can have a peak molecular weight from about 4,000 g/mol to about 30,000 g/mol, or alternatively from about 5,000 g/mol to about 15,000 g/mol.

The (B) blocks of the conjugated diene can be 1,3-butadiene and substituted butadiene such as isoprene, piperylene, 2,3-dimethyl-1,3-butadiene, and 1-phenyl-1,3-butadiene, or combinations thereof. In an aspect, the B block of polymerized conjugated diene comprises polymerized isoprene. The B blocks can have a peak molecular weight from about 20,000 g/mol to about 200,000 g/mol, or alternatively from about 40,000 g/mol to about 120,000 g/mol.

The optional C block(s) of polymerized conjugated diene can be 1,3-butadiene and substituted butadiene such as isoprene, piperylene, 2,3-dimethyl-1,3-butadiene, and 1-phenyl-1,3-butadiene, or combinations thereof. In an aspect, the (C) block(s) of polymerized conjugated diene comprise butadiene. The C block can have a peak molecular weight of about 2000 g/mol to about 30,000 g/mol, or alternatively from about 2000 g/mol to about 10,000 g/mol.

In an aspect, the molecular weight of the B block is greater than or equal to the molecular weight of the C block. When employing a coupling agent there will be a triblock of the type C-A-B or a diblock of the type A-B. The triblock or diblock may be present in the block copolymer (component 1) in an amount of from between about 5 wt. % to about 35 wt. % based on the total weight of the block copolymer.

The melt flow range of the block copolymer (component 1) can be from about 20 g/10 min. to about 100 g/10 min. at conditions of 200° C. under a 5 kg mass. In an alternative aspect, the melt flow rate is about 30 g/10 min. to about 40 g/10 min. at the conditions of 200° C. under a 5 kg mass.

In an aspect, the structure of the block copolymer (component 1) has at least one internal B block in the structure and one terminal A block in the structure. In an alternative aspect, the structure of the block copolymer (component 1) is at least one internal B block in the structure and one terminal C block in the structure (e.g., A-B-A-C or C-A-B-A-C). In such aspects, structures having a terminal C block, the C block may have a smaller molecular weight than any internal B block.

In the block copolymers according to the present disclosure (component 1), the poly(styrene) content (which may include optional co-monomers) is in the range of from about 28 wt. % to about 50 wt. %, alternatively from about 28 wt. % to about 35 wt. %, or alternatively from about 29 wt. % to about 33 wt. based on the total weight block copolymer (i.e., component 1).

The block copolymers to be applied in the adhesive compositions according to the present disclosure (component 1) have a number average molecular weight ($M_n$ expressed in terms of polystyrene) ranging from about 150,000 g/mol to about 500,000 g/mol, or alternatively from about 100,000 g/mol to about 230,000 g/mol, as determined by gel permeation chromatography (GPC, using the method described by RUNYON, James R. et al., Multiple detectors for molecular weight and composition analysis of copolymers gel permeation chromatography (Journal of Applied Polymer Science, 1969, vol. 13, no, 11, p. 2359-69).

As used herein, the term "molecular weights" refers to the true molecular weight in g/mol of the polymer or block of the copolymer. The molecular weights referred to in this specification and claims can be measured with gel permeation chromatography (GPC) using polystyrene calibration standards, such as is done according to ASTM D5296. GPC is a method wherein polymers are separated according to molecular size, the largest molecule eluting first. The chromatograph is calibrated using commercially available polystyrene molecular weight standards. The molecular weight of polymers measured using GPC so calibrated are styrene equivalent molecular weights. The styrene equivalent molecular weight may be converted to true molecular weight when the styrene content of the polymer and the vinyl content of the diene segments are known. The detector used is preferably a combination ultraviolet and refractive index detector. The molecular weights expressed herein are measured at the peak of the GPC trace, converted to true molecular weights, and are commonly referred to as "peak molecular weights".

In an aspect of this disclosure, block copolymers (component 1) with structures having terminal C block(s) (e.g., C-A-B-A-C) have a molecular weight ratio of the terminal C block to that of internal B block(s) of from about 0.01:1 to about 1:1, or alternatively from about 0.05:1 to about 0.1:1. In another aspect of this disclosure, block copolymers (component 1) with structures having terminal C block(s) (e.g., C-A-B-A-C) have a molecular weight of the terminal C block to that that is from about 1% to about 20% of the molecular weight of the internal B block(s).

In an aspect, the terminal block resin is a high $T_g$, low MW styrenic resin (e.g., alpha-methyl styrene resin) that increases the creep performance. Examples of commercially available resins for the terminal block resin include without limitation KRISTLEX 3085.

The block copolymers of the present disclosure (component 1) have a melt flow index measured at 200° C. under 5 kg mass in accordance with ASTM D-1238 ranging from about 18 g/10 min. to about 100 g/10 min. The melt flow rate within this range will generally provide the hot-melt adhesive of the present disclosure with viscosities below about 10,000 cps at about 130° C. It is observed that hot-melt adhesive viscosities below about 10,000 cps at about 130° C. are sprayable at temperatures in the range of about 125° C., to about 138° C.

The block copolymers of the present disclosure (component 1) may be created sequentially or by coupling as noted in reissued U.S. Pat. No. RE 27,145, hereby incorporated by reference. Sequentially means that each block copolymer is prepared by anionic polymerization starting with a terminal block polymer (polymerizing the monomer into a block polymer) and then attaching that to the next monomer being polymerized into a block polymer, (thus forming a copolymer) until the desired structure is complete. When the block copolymers according to the present disclosure are made by coupling living block copolymers with a coupling agent, various block copolymers are joined together via the coupling agent. The coupling agent includes any chemical species having multiple functionalities and reactive with the living anionic chain-end in an additive fashion.

Suitable coupling agents are dihalo alkanes, silicon halides, siloxanes, multifunctional epoxides, silica compounds, esters of monohydric alcohols with carboxylic acids, and epoxidized oils. Other nonlimiting examples of coupling agents include divinylbenzene, tetra-alkoxysilanes, such as include tetra-ethoxysilane and tetra-methoxysilane, alkyl-trialkoxysilanes including methyl-trimethoxy silane, aliphatic diesters including dimethyl adipate and diethyl adipate, and diglycidyl aromatic epoxy compounds including diglycidyl ethers deriving from the reaction of bisphenol A and epichlorohydrin.

In an aspect, the block copolymer (component 1) is present in the composition in an amount of from about 10 wt. % to about 60 wt. %, alternatively from about 18 wt. % to about 50 wt. % based on the total weight of the adhesive formulation.

The tackifying resins (component 2) to be used in the hot melt adhesive compositions of the present disclosure can be any resin compatible with the other components of the hot-melt adhesives. The resins can be selected from modified aliphatic hydrocarbon resins such as modified $C_5$ hydrocarbon resins ($C_5$/$C_9$ resins), styrenated terpene resins, fully or partially hydrogenated $C_9$ hydrocarbon resins, hydrogenated cycloaliphatic hydrocarbon resins, hydrogenated aromatic modified cycloaliphatic hydrocarbon resins, and combinations thereof.

Examples of tackifying resins to be used as component (2) include, but are not limited to: water white hydrocarbon resins of the ESCOREZ™ resin series such as ESCOREZ™ 5600, ESCOREZ™ 5400, ESCOREZ™ 5300 and the like commercially available from Exxon Mobil Chemical Co., or hydrocarbon resins of the REGALITE™ resin series such as REGALITE™ 1090, REGALITE™ 7100 and REGALITE™ S-5100 resins and the like, or the EASTOTAC™ resin series, such as EASTOTAC™ 100W and the like both of which are commercially available from Exxon Mobil Chemical Co., or the ARKON™ resin series, like ARKON™ P and M resin, commercially available from Arakawa Chemical Company.

In an aspect, the one or more tackifying resins are solid tackifying resins with a Ring and Ball softening point in the range of from about 90° C. to about 105° C. and will have an aromatic proton nuclear magnetic resonance (H-NMR) content from 0 to about 30%, or alternatively from 0 to about 12%.

In the hot-melt adhesive compositions of the present disclosure, the one or more tackifying resins component (2) are present in an amount from about 35 wt. % to about 60 wt. % based on 100 wt. % of the hot-melt adhesive composition or in other words based on the total weight of the hot-melt adhesive composition. In an alternative aspect, component (2) is present in an amount of from 40 wt. % to 50 wt. % based on the total weight of the hot-melt adhesive composition.

Suitable plasticizers (component 3) include predominantly plasticizing oils that are paraffinic or naphthenic in character such as a carbon aromatic distribution less than or equal to about 5%, alternatively less than or equal to about 2%, alternatively 0% as determined according to DIN 51378 and a glass transition temperature less than about −55° C. or alternatively less than about −65° C. as measured by Differential Scanning Calorimetry. Examples of plasticizers (component 3) suitable for use in the present disclosure are commercially available from the Royal Dutch/Shell Group of companies, such as SHELLFLEX™, CATENEX™, and ONDINA™ oils. Other oils include KAYDOL™ oil from Witco, TUFFLO™ oils from Arco, NYPLAST™ from NYNAS, or CALSOL™ 5550 or 5555 from CALUMET LUBRICANTS, or Sontex™ 450 or Nyflex™ 22213 or Drake oil from Penreco Co.

Other plasticizers may also be included in the hot-melt adhesive composition, such as olefin oligomers; low molecular weight polymers (less than or equal to 30,000 g/mol) such as liquid polybutene, liquid polyisoprene copolymers, liquid styrene/isoprene copolymers or liquid hydrogenated styrene/conjugated di ene copolymers; vegetable oils and their derivatives; or paraffin and microcrystalline waxes.

The hot-melt adhesive composition according to the present disclosure comprises a plasticizer (component 3) present in an amount of from about 10 wt. % to about 25 wt. %, based on the total weight of the hot-melt adhesive composition.

It will be appreciated that each block copolymer of component (1) may be pre-blended with a small amount of plasticizer by the manufacturer of said copolymer. This small amount aids in the flowability of the block copolymer. This small amount, if present, is included in the overall calculation of the amount of plasticizer.

The hot-melt adhesives of the present disclosure may further comprise an antioxidant (component 4). Most antioxidants fall into the category of primary or secondary antioxidants and have different functions due to different chemical structures. A primary antioxidant is typically a hindered phenol or arylamines. Primary antioxidants scavenge alkoxy radicals and peroxy radicals. Any primary antioxidant compatible with styrenic block copolymers may be incorporated into the compositions of the present disclosure. Primly antioxidants sold under the trade name. IRGANOX from BASF may be suitable for use in the present disclosure, such as 1010, 1076, and 1330.

Secondary antioxidants may also be used along with the primary antioxidants. Secondary antioxidants are typically phosphites and thiosynergists. Secondary antioxidants scavenge hydroperoxides which are generated during the autoxidation cycle of a polymer exposed to heat and oxygen. Various compositions sold under the trade name, IRGAFOS™, may be suitable and are likewise manufactured by BASF. IRGAFOS™ 168 and the like may be suitable for the present disclosure carbon radical scavengers. Examples of carbon radical scavengers suitable for use in the present disclosure are commercially available under the tradename SUMILIZER™, produced by Sumitomo Chemical.

Antioxidants can also be added to protect the adhesive from degradation induced by heat, light and processing. Several types of antioxidants can be used, either primary antioxidants like hindered phenols or secondary antioxidants like phosphite derivatives or blends thereof.

Other examples of commercially available antioxidants include IRGANOX® 565 from Ciba-Geigy (2.4-bis-(n-octylthio)-6-(4-hydroxy-3,5-di-tertiary-butyl anilino)-1,3,5-triazine), IRGANOX™ 1010 from Ciba-Geigy (tetrakis-ethylene-(3,5-di-tertiary-butyl-4-hydroxy-hydrocinnamate) methane) and POLYGARD™ HR from Uniroyal (tris-(2,4-di-tertiary-butyl-phenyl)phosphite). Other antioxidants developed to protect the gelling of the polybutadiene segments can also be used, such as SUMILIZER™ GS from Sumitomo (2[1-(2-hydroxy-3,5-di-ter-pentylphenyl)ethyl)]-4,6-di-tert-pentyl phenyl acrylate); SUMILIZER™ T-PD from Sumitomo (pentaerythrythyltetrakis(3-dodecylthiopropionate)); or combinations thereof.

The one or more antioxidants are optionally present in an amount from about 0.01 wt. % to about 2 wt. % of antioxidants based on the total weight of the hot-melt adhesive composition. In an alternative aspect of the present disclosure, component (4) is present in an amount of from about 0.5 wt. % to about 1.5 wt. %, based on the total weight of the hot-melt adhesive composition.

In an aspect, the alkenyl arene homo or copolymer (component 5), if present, is present in an amount of equal to or less than about 35 wt. % based on the total weight of the hot-melt adhesive composition. Alternatively, the alkenyl arctic homo or copolymer (component 5), if present, is present in an amount of from about 20 wt. % to about 25 wt. %. Examples of commercially available alkenyl arene homo or copolymer (component 5) suitable for use in the present disclosure include ENDEX™ 155 or 160, KRISTALEX™ 3085 and the like which are commercially available from the Eastman Chemical Co. which are predominantly alpha methyl styrene.

No particular limitation is imposed on the preparation process of the hot-melt adhesive compositions of the present disclosure. Therefore, any process may be used to combine components 1-4 (or 1-5) of the hot-melt adhesive composition, such as a mechanically mixing process making use of rolls, a Banbury mixer or a Dalton kneader. Other methods for combining the components of the hot melt adhesive include a hot-melt process characterized in that heating and mixing are conducted by using a melting kettle equipped with a stirrer, such as a turbo-mixer, a high shear Z-blade mixer or a single- or twin-screw extruder, or a solvent process in which the compounding components are poured in a suitable solvent and stirred, thereby obtaining an intimate solution of the pressure sensitive adhesive composition (aka the hot melt adhesive composition).

A variety of other rubber components may be incorporated into the hot-melt adhesive compositions of the present disclosure as desired to modify the tack, the odor, or the color of the hot melt adhesive. Hot-melt adhesive compositions according to the present disclosure are efficiently applied as assembly adhesive compositions or as attachment adhesive compositions for assembling (e.g., as described herein) sanitary articles, in particular diapers, comprising a polyethylene framework and at least one non-woven lining element.

The following advantages of the formulated hot-melt adhesive compositions according to the present disclosure have been found to display improved creep properties in elastic fiber adhesion; and good sprayability, even at low temperatures.

EXAMPLES

The following examples are provided to illustrate the present disclosure. The examples are not intended to limit the scope of the present disclosure and they should not be so interpreted.

Three versions of the styrene/isoprene multi block copolymers were prepared (similar molecular weights but varying melt flow rates and their characteristics presented in Table 1.

TABLE 1

| Sample Designation | Polystyrene block 1 Approximate $M_n$ (kDa) | Polystyrene block 2 Approximate $M_n$ (kDa) | Rubber Block B + C Approximate $M_n$ (kDa) |
|---|---|---|---|
| F-436 | 15 | 13 | 64 |
| Campaign 25 | 15 | 14 | 72 |
| Campaign 55 | 15 | 14 | 61 |
| Kraton ™ D1165 (A) | 15 | 15 | 80 |

The first synthesis was carried out in a small scale pilot reactor and resulted in the model block copolymer called F-436. Afterwards there were two large scale samples (approximately 230 kg scale) samples made from a semi commercial reactor system, referred to as campaigns 25 and 55. This resulted in three variations; the campaign 55 material having the best balance of properties in terms of high melt flow rate and tensile strength. Comparative data is given in Table 2.

TABLE 2

| Polymer | Location Produced | Melt Flow Rate, g/10 min at 200° C./ 5 kg | Tensile Strength*** of compression molded sample (psi) | Elastic Attachment Laminate Testing |
|---|---|---|---|---|
| F-436 | Pilot | 26 | 3830 | No, sample size too small |
| Campaign-25 | Semi-commercial scale | 18 | 2230 | Yes |

TABLE 2-continued

| Polymer | Location Produced | Melt Flow Rate, g/10 min at 200° C./ 5 kg | Tensile Strength*** of compression molded sample (psi) | Elastic Attachment Laminate Testing |
|---|---|---|---|---|
| Campaign-55 | Semi-commercial scale | 36 | 3715 | Yes, best overall performing version |
| Comparative A | Commercial scale | 7 | 1735 | Yes (see Table 5) |

***Tensile test conditions: ASTM D 412 type D die, gauge length = 1", x-head speed = 10"/min, 50 lb load cell, see Appendix 3.0

Adhesive Performance

Table 3 presents the starting point formulations used to screen the hot-melt viscosities of Campaign-55 and Comparative A. These formulations were mixed in a sigma blade mixer at 160° C.

Figure 2:
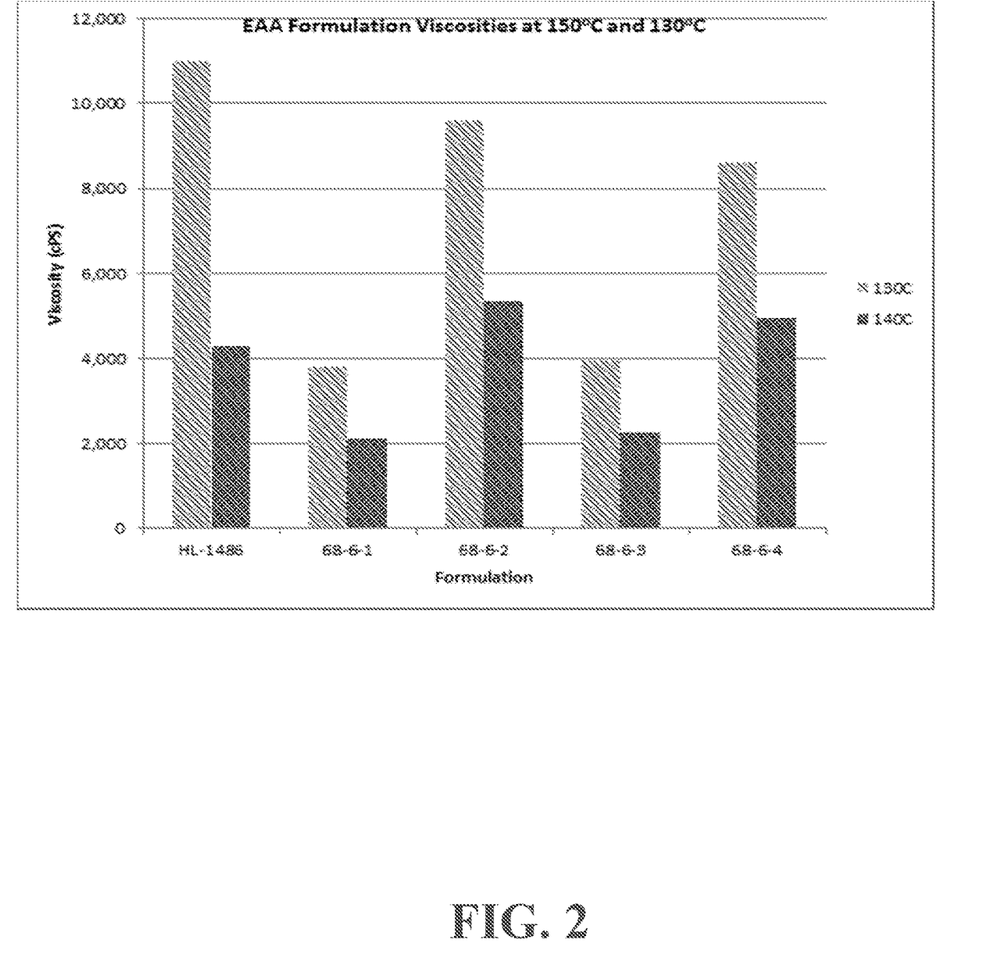
FIG. 2 is a plot of hot-melt viscosity vs. temperature performance at 20 wt. % polymer content.

FIG. 2 reveals the resultant hot-melt viscosity vs. temperature performance at 20% polymer content. Indeed campaign-55 met the criteria for low hot-melt viscosity all the way down to 120° C.

TABLE 3

| Material, wt. % | F1 | F2 | F3 | F4 | F5 | F6 |
|---|---|---|---|---|---|---|
| Campaign-55 (MFR~36) | 20 | 15 | | | | |
| Campaign 25 (MFR~18) | | | 20 | 15 | | |
| Comparative A | | | | | 20 | 15 |
| Eastotac 100W midblock resin | 45 | 45 | 45 | 45 | 45 | 45 |
| Kristalex 3085 end-block resin | 20 | 25 | 20 | 25 | 20 | 25 |
| Sontex 450 oil | 14.9 | 14.9 | 14.9 | 14.9 | 14.9 | 14.9 |
| Irganox 1010 | 0.1 | 0.1 | 0.1 | 0.1 | 0.1 | 0.1 |
| SAFT to Mylar (2.54 cm square, 0.5 kg), (° C.) | 69 | 60 | 73 | 69 | 79 | 73 |

Figure 1:
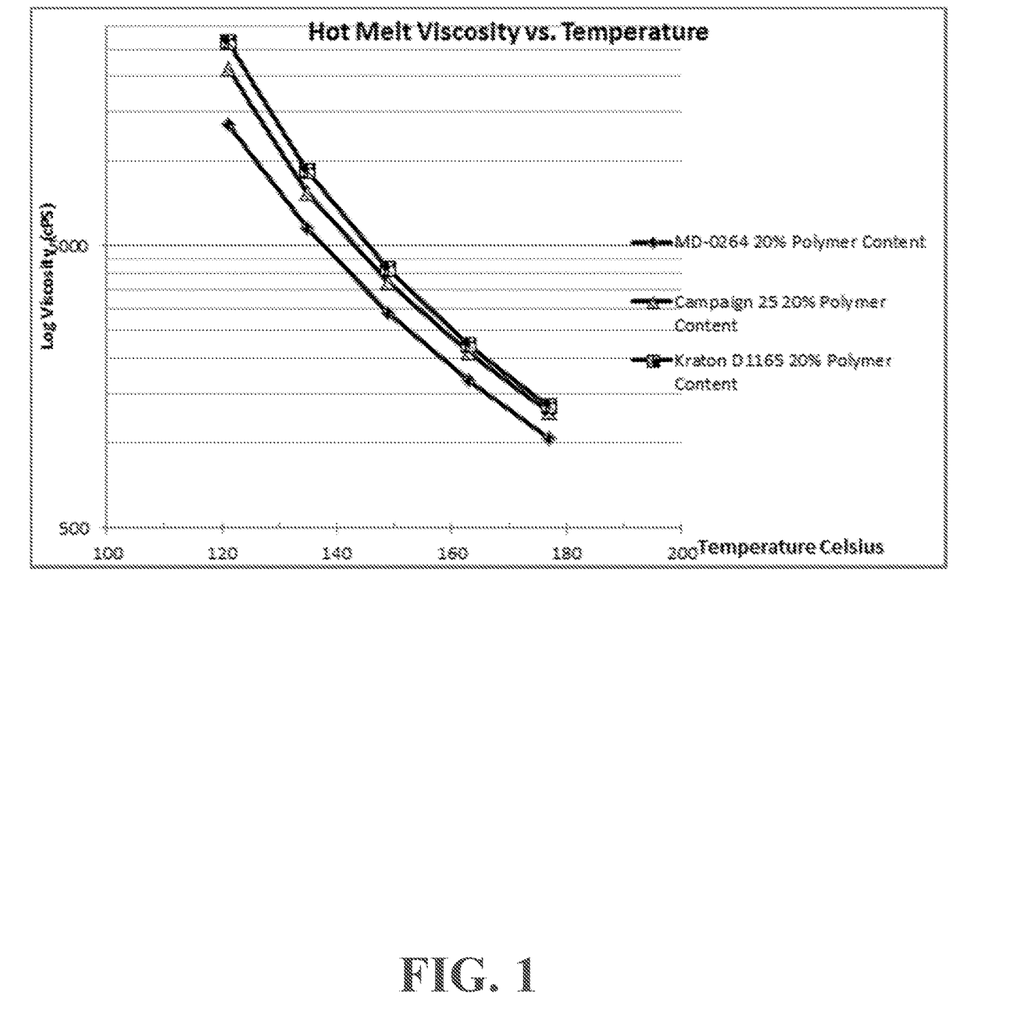
FIG. 1 is a plot of hot-melt viscosity vs. temperature for formulations at the 20 wt. % polymer content.

The shear adhesion temperature failure (SAFT) to Mylar of each hot-melt formulation was examined for an indication of shear resistance at higher temperatures. The lower viscosity formulations did show lower SAFT indicating that the structural change that benefits viscosity has some trade-off with this property (this data is given in Table 3). Since the EAA laminate needs to function at only at body temperature (i.e., 37° C.), the lower SAFT may not be an issue. When Holding Power (HP) was examined (a similar shear test to SAFT, but at 25° C.), HP to stainless steel was greater than 10,000 minutes for all the formulations (including with 15% polymer content) which is excellent performance. FIG. 1 is a plot of hot-melt viscosity vs. temperature for formulations at the highest polymer content (see Table 3). From this plot it is clear that Campaign-55 has the lowest viscosity at the temperature range shown, with a 20 wt. % loading of polymer.

Samples of Campaign-55 were further evaluated by producing the elastic laminate. 2.0 Kilogram scale formulations were prepared that were then used for the spray trials in elastic laminate production. It should be noted that the two control formulations could not be spray applied at temperatures below 150° C. Comparative A had higher creep compared to the styrene-isoprene-styrene based commercially available block copolymer. Creep was determined as follows: six constructs were cut to dimensions of approximately 25 mm wide and 400 mm long. One end was stapled to a testing cardboard that had been marked with three sets of lines. The first line was the zero line which was located approximately 15 mm from one edge of the cardboard. The second line was 285 mm from the zero line and the third line was 300 mm from the zero line and approximately 15 mm on the opposite edge of the cardboard from the zero line. The first end of the construct is stapled between the zero line and the edge of the cardboard within the 15 mm. The construct was then stretched to full extension leaving no gathers in the laminate and then marked with a pen at the 300 mm mark. The construct was then relaxed until the mark was over the 285 mm line. This left the construct stretched to 95% of the full extension. After a complete set had been fastened, a razor blade was then used to cut through each of the elastic threads on both ends. One set of cuts was made at the zero line and the other at the 285 mm line. The test board was then placed in a forced air oven set at 100±1° F. for a period of four hours. After four hours the test board was removed and the marks placed on each end of the construct where the elastic threads were no longer gathering the film and fabric. Each mark represented an average of three strands of elastic for each end. The distance between the two marks was then measured and the % creep calculated using the formula % creep=Initial(285)−Final/Initial(285)×100.

TABLE 4

| Ingredients Wt. % | HL-1486 Commercial* | Sample 1 | Sample 2 | Sample 3 |
|---|---|---|---|---|
| Block Copolymer | NA | 20 | 15 | 15 |
| Kristalex 3085 | NA | 15 | 25 | 15 |
| Endex 160 (RBSP~160° C.) | NA | 5 | | 5 |
| Eastotac H100 | NA | 45 | 45 | 50 |
| Nyflex 222B | NA | 14.5 | 14.5 | 14.5 |
| Irganox 1010 | NA | 0.5 | 0.5 | 0.5 |

*H.B. Fuller, SIS based but composition is unknown

FIG. 2 is a plot of hot-melt viscosities for EAA formulations mixed for spray lamination trials—Formulations HL1486 (commercial control), 68-6-2 and 68-6-4 were chosen for the final lamination trials.

TABLE 5

| Sample No. | Appl. Temp. (° C.) | Coat Weight (gsm CF or mg/lm/ strand SW) | Creep Average 32" Nip | Std. Deviation 32" Nip | Avg. 19.25" Nip | Std. Deviation 19.25" Nip | % Improvement by decreasing Nip distance |
|---|---|---|---|---|---|---|---|
| HL1486 control | 160 | 50 | 8.3% | 0.0256 | 3.1% | 0.0031 | 5.2% |
| Comparative A | 160 | 50 | 13.9 | 0.0233 | NT | NT | NA |
| Sample 4 | 130 | 50 | NT* | NT | 31.8% | 0.0870 | NA |
| Sample 4 | 140 | 50 | NT | NT | 34.7% | 0.6509 | NA |
| Sample 4 | 150 | 50 | NT | NT | 9.0% | 0.0093 | NA |

TABLE 5-continued

| Sample No. | Appl. Temp. (° C.) | Coat Weight (gsm CF or mg/lm/ strand SW) | Creep Average 32" Nip | Std. Deviation 32" Nip | Avg. 19.25" Nip | Std. Deviation 19.25" Nip | % Improvement by decreasing Nip distance |
|---|---|---|---|---|---|---|---|
| Sample 2 | 130 | 50 | 70.8% | 0.1226 | 50.6% | 0.1408 | 20.2% |
| Sample 2 | 140 | 50 | 66.1% | 0.0930 | 50.2% | 0.0819 | 15.9% |
| Sample 2 | 150 | 50 | 13.0% | 0.0253 | 7.8% | 0.0177 | 5.3% |

*Not Tested - these were new formulations that were not previously tested at 32" Nip distance As the base polymer for EAA formulations, Campaign-55 had the following observed benefits vs. Comparative A:
Lower melt viscosity
Higher tensile strength (although SAFT was lower vs. Comparative A as an adhesive)
Neither the Comparative A control nor the commercial HL1486 formulations could be spray-applied below 150° C.
Changes in open time (nip spacing) improve the creep performance at the lowest application temperature.

Thus it is apparent that there has been provided, in accordance with the disclosure, an adhesive composition, a diaper, and a method of constructing a diaper that fully satisfies the objects, aims and advantages set forth above. While the disclosure has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

ADDITIONAL DISCLOSURE

The following enumerated aspects of the present disclosures are provided as nonlimiting examples.

A first aspect which is an adhesive composition comprising one or more block copolymers and one or more tackifying resins, wherein said one or more block copolymers comprise (i) one or more blocks of polymerized alkenyl arene monomer (A block), (ii) one or more blocks of polymerized conjugated diene monomer (B block), and optionally at least one low molecular weight (compared to B block) block of polymerized conjugated diene (C block), where the A, B, and C blocks can vary independent of each other with regard to composition and molecular weight.

A second aspect which is the adhesive composition of the first aspect wherein the block copolymer has a structure selected from the group A-B-A; (AB)nX, A-B-A-C, C-A-B-A-C, (C-A-B)nX, (A-B)nX(C)m, and (C-A-B)nX(C)m where n and/or m is from 2 to 20, X is a coupling agent and the sum of n+m cannot be greater than the valence of the coupling agent, A third aspect which is the adhesive composition of any of the first through second aspects wherein the alkenyl arene monomer is styrene, alpha-methylstyrene, para-methylstyrene, vinyl toluene, vinyl naphthalene, para-butyl styrene or combinations thereof.

A fourth aspect which is the adhesive composition of third aspect wherein the alkenyl arene monomer is styrene.

A fifth aspect which is the adhesive composition of any of the first through fourth aspects wherein the conjugated diene monomer is 1,3-butadiene, a substituted butadiene, isoprene, piperylene, 2,3-dimethyl-1,3-butadiene, 1-phenyl-1,3-butadiene, or combinations thereof.

A sixth aspect which is the adhesive composition of any of the first through fifth aspects wherein the conjugated diene monomer is isoprene.

A seventh aspect which is the adhesive composition of any of the first through sixth aspects wherein the coupling agent comprises any chemical species having multiple functionalities and reactive with the living anionic chain-end in an additive fashion.

An eighth aspect which is the adhesive composition of any of the first through seventh aspects, wherein the A blocks have a peak molecular weight from about 4,000 g/mol to about 30,000 g/mol.

A ninth aspect which is the adhesive composition of the eighth aspect wherein the B blocks have a peak molecular weight from about 20,000 g/mol to about 200,000 g/mol.

A tenth aspect which is the adhesive composition of the ninth aspect wherein the C blocks have a peak molecular weight from about 2,000 g/mol to 30,000 g/mol.

An eleventh aspect which is the adhesive composition of the ninth aspect wherein structures having terminal C block(s) have a molecular weight ratio to that of internal B block(s) of 0.01:1 to 1:1.

A twelfth aspect which is the adhesive composition of the tenth aspect wherein the molecular weight ratio of terminal C block(s) to internal B block(s) have a ratio of from 0.05:1 to 0.1:1.

A thirteenth aspect which is the adhesive composition of any of the first through twelfth aspects wherein the structures have at least one terminal C block in the structure and one terminal A block in the structure.

A fourteenth aspect which is the adhesive composition of the any of the first through thirteenth aspects wherein the structures having a terminal C block have a smaller molecular weight than any internal B block.

A fifteenth aspect which is the adhesive composition of any of the first through fourteenth aspect further comprising: one or more end block resins and one or more oils, wherein the block copolymer is present in a range from about 15 wt. % to about 50 wt. %, the tackifier is present in a range from about 35 wt. % to about 60 wt. %, the one or more end block resins are present in a range of about 0 to about 35 wt. %, and the one or more oils are present in a range of about 10 wt. % to about 25 wt. %, based on the total weight of the adhesive composition.

A sixteenth aspect which is the adhesive composition of any of the first through fifteenth aspects further comprising from about 0.01 wt. % to about 2 wt. % of one or more primary antioxidants and from about 001 wt. % to about 2 wt. % of a secondary antioxidant based on the total weight of the adhesive composition.

A seventeenth aspect which is the adhesive composition of any of the first through sixteenth aspect wherein the adhesive is a hot-melt adhesive for an elastic attachment. In an embodiment the composition has a creep of 30% or less;

SAFT of 30° C. to 60° C.; a melt flow rate measured at 200° C. under 5 kg mass in accordance with ASTM D-1238 ranging from about 10 g/10 min. to about 50 g/10 min; a tensile strength of from about 1,000 psi to about 5,000 psi determined according to ASTM D 412.

An eighteenth aspect which is a process of the using the adhesive composition of the sixteenth aspect wherein the adhesive is sprayed on an elastic attachment and allowed to dry.

A nineteenth aspect which is the process of the sixteenth aspect wherein the adhesive is sprayed on the elastic attachment at a temperature between about 125° C. to 138° C.

A twentieth aspect which is the process of any of the eighteenth through nineteenth aspects wherein the adhesive is sprayed onto the elastic attachment of a diaper at a temperature of between about 130° C. to about 135° C.

A twenty-first aspect which is a diaper having leg and waist holes for humans comprising elastic attachments around the leg and waist holes of the diaper, the elastic attachment being secured to the diaper by means of an adhesive composition, the adhesive composition comprising one or more block copolymers wherein said one or more block copolymers comprise (1) one or more blocks of polymerized alkenyl arene monomer (A block), (ii) one or more blocks of polymerized conjugated diene monomer (B block), and optionally at least one low molecular weight (compared to B block) block of polymerized conjugated diene (C block), where the A. B, and C blocks can vary independent of each other with regard to composition and molecular weight, one or more end block resins, one or more tackifiers, and one or more oils, wherein the block copolymer is present in a range from about 10 to about 30 wt. %, the tackifier is present in a range from about 25 wt. % to about 70 wt. %, the one or more end block resins are present in a range of about 10 wt. % to about 40 wt. %, and the one or more oils are present in a range of about 5 wt. % to about 30 wt. % based on the total weight of the adhesive composition.

A twenty-second aspect which is the diaper of the twenty-first aspect wherein the A blocks have a peak molecular weight from about 4.000 wt % to about 30,000 g/mol.

A twenty-third aspect which is the diaper of any of the twenty-first through twenty-second aspects wherein the B blocks have a peak molecular weight from about 20,000 g/mol to about 200,000 g/mol.

A twenty-fourth aspect which is the diaper of any of the twenty-first through twenty-third aspects wherein structures having terminal C block(s) have a molecular weight ratio to that of internal B block(s) of from 0.01:1 to 1:1.

A twenty-fifth aspect which is the diaper of any of the twenty-first through twenty-fourth aspects wherein the ratio of terminal C block(s) to internal B block(s) have a ratio of from 0.05:1 to 0.1:1.

What is claimed is:

1. An adhesive composition comprising: one or more block copolymers and one or more tackifying resins, wherein said one or more block copolymers comprise (i) one or more blocks of polymerized alkenyl arene monomer (A block), (ii) one or more blocks of polymerized conjugated diene monomer (B block), and at least one low molecular weight (compared to B block) block of polymerized conjugated diene (C block), where the A, B, and C blocks can vary independent of each other with regard to composition and molecular weight;

wherein the block copolymer has a structure selected from the group consisting of A-B-A-C, C-A-B-A-C, (C-A-B)$_n$X, (A-B)$_n$X(C)$_m$, and (C-A-B)$_n$X(C)$_m$;

where the one or more A blocks have a peak molecular weight from 10,000 g/mol to 25,000 g/mol; the one or more B blocks have a peak molecular weight from 40,000 g/mol to 120,000 g/mol; the molecular weight of the C block is from 1% to 40% of the molecular weight of the B block; and each of n and m is from 2 to 20, X is a coupling agent, and (n+m) cannot be greater than the valence of the coupling agent;

and wherein the adhesive composition has
   a creep of 30% or less;
   a shear adhesion failure temperature of 30° C. to 60° C.;
   a melt flow rate of 10 g/10 min to 50 g/10 min, measured at 200° C., under 5 kg mass in accordance with ASTM D-1238;
   and a tensile strength of from 1,000 psi to 5,000 psi determined according to ASTM D 412.

2. The adhesive composition of claim 1, wherein the alkenyl arene monomer is styrene, alpha-methylstyrene, para-methylstyrene, vinyl toluene, vinyl naphthalene, para-butyl styrene or combinations thereof.

3. The adhesive composition of claim 2, wherein the alkenyl arene monomer is styrene.

4. The adhesive composition of claim 1, wherein the conjugated diene monomer is 1,3-butadiene, a substituted butadiene, isoprene, piperylene, 2,3-dimethyl-1,3-butadiene, 1-phenyl-1,3-butadiene, or combinations thereof.

5. The adhesive composition of claim 1, wherein the conjugated diene monomer is isoprene.

6. The adhesive composition of claim 1, wherein the coupling agent comprises any chemical species having multiple functionalities and reactive with the living anionic chain-end in an additive fashion.

7. The adhesive composition of claim 1, wherein the C blocks have a peak molecular weight from about 2,000 g/mol to 30,000 g/mol.

8. The adhesive composition of claim 7, wherein the molecular weight ratio of terminal C block(s) to internal B block(s) have a ratio of from 0.05:1 to 0.1:1.

9. The adhesive composition of claim 1, wherein the structures have at least one terminal C block in the structure and one terminal A block in the structure.

10. The adhesive composition of claim 1, further comprising: one or more end block resins and one or more oils, wherein the block copolymer is present in a range from about 15 wt. % to about 50 wt. %, the tackifier is present in a range from about 35 wt. % to about 60 wt. %, the one or more end block resins are present in a range of about 0 to about 35 wt. %, and the one or more oils are present in a range of about 10 wt. % to about 25 wt. %, based on the total weight of the adhesive composition.

11. The adhesive composition of claim 1, further comprising from about 0.01 wt. % to about 2 wt. % of one or more primary antioxidants and from about 0.01 wt. % to about 2 wt. % of a secondary antioxidant based on the total weight of the adhesive composition.

12. The adhesive composition of claim 1, wherein the adhesive is a hot-melt adhesive for an elastic attachment.

13. A process of using the adhesive composition of claim 11, wherein the adhesive is sprayed on an elastic attachment and allowed to dry.

14. The process of claim 13, wherein the adhesive is sprayed on the elastic attachment at a temperature between about 125° C. to about 138° C.

15. The process of claim 13, wherein the adhesive is sprayed onto the elastic attachment of a diaper at a temperature of between about 130 to about 135° C.

16. A diaper having leg and waist holes for humans comprising elastic attachments around the leg and waist holes of the diaper, the elastic attachment being secured to the diaper by means of an adhesive composition, the adhesive composition comprising:
- one or more block copolymers wherein said one or more block copolymers comprise
  - (i) one or more blocks of polymerized alkenyl arene monomer (A block),
  - (ii) one or more blocks of polymerized conjugated diene monomer (B block), and
  - (iii) at least one low molecular weight (compared to B block) block of polymerized conjugated diene (C block), where the A, B, and C blocks can vary independent of each other with regard to composition and molecular weight;
- wherein the block copolymer has a structure selected from the group consisting of A-B-A-C, C-A-B-A-C, (C-A-B)$_n$X, (A-B)$_n$X(C)$_m$, and (C-A-B)$_n$X(C)$_m$; where each of n and m is from 2 to 20, X is a coupling agent, and (n+m) cannot be greater than the valence of the coupling agent;
- where the one or more A blocks have a peak molecular weight from 10,000 g/mol to 30,000 g/mol; the one or more B blocks have a peak molecular weight from 40,000 g/mol to 120,000 g/mol; the molecular weight of the C block is from 1% to 40% of the molecular weight of the B block; and n and/or m is from 2 to 20, X is a coupling agent, and (n+m) cannot be greater than the valence of the coupling agent;
- one or more end block resins,
- one or more tackifiers,
- and one or more oils,
  - wherein the block copolymer is present in a range from about 10 to about 30 wt. %, the tackifier is present in a range from about 25 wt. % to about 70 wt. %, the one or more end block resins are present in a range of about 10 wt. % to about 40 wt. %, and the one or more oils are present in a range of about 5 wt. % to about 30 wt. % based on the total weight of the adhesive composition;
  - and wherein the adhesive composition has a creep of 30% or less; a shear adhesion failure temperature of 30° C. to 60° C.; a melt flow rate of 10 g/10 min to 50 g/10 min, measured at 200° C., under 5 kg mass in accordance with ASTM D-1238; and a tensile strength of from 1,000 psi to 5,000 psi determined according to ASTM D 412.

* * * * *